(12) United States Patent
Yardibi et al.

(10) Patent No.: US 11,849,932 B2
(45) Date of Patent: Dec. 26, 2023

(54) SENSOR ENABLED RETRACTOR FOR ROBOTIC SURGERY

(71) Applicant: DePuy Ireland Unlimited Company, Ringaskiddy (IE)

(72) Inventors: Tarik Yardibi, Wayland, MA (US); Robert Brik, Brookline, MA (US); Brice Dudley, Jr., Round Rock, TX (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 181 days.

(21) Appl. No.: 17/366,427

(22) Filed: Jul. 2, 2021

(65) Prior Publication Data

US 2022/0015750 A1 Jan. 20, 2022
US 2022/0175358 A2 Jun. 9, 2022

Related U.S. Application Data

(60) Provisional application No. 63/051,863, filed on Jul. 14, 2020.

(51) Int. Cl.
*A61B 17/02* (2006.01)
*A61B 34/30* (2016.01)
*A61B 90/50* (2016.01)
*A61B 90/00* (2016.01)
*A61B 17/00* (2006.01)

(52) U.S. Cl.
CPC ............. *A61B 17/02* (2013.01); *A61B 34/30* (2016.02); *A61B 90/50* (2016.02); *A61B 2017/00022* (2013.01); *A61B 2017/0262* (2013.01); *A61B 2090/065* (2016.02)

(58) Field of Classification Search
CPC ......... A61B 17/02; A61B 34/30; A61B 90/50; A61B 2017/00022; A61B 2090/065
USPC ............................ 600/201–245; 606/201–245
See application file for complete search history.

(56) References Cited

U.S. PATENT DOCUMENTS

2018/0132839 A1\* 5/2018 Friedrich ............... A61B 34/76
2021/0186477 A1\* 6/2021 Buehlmann ........ A61B 17/7074

\* cited by examiner

*Primary Examiner* — Eduardo C Robert
*Assistant Examiner* — Tara Rose E Carter
(74) *Attorney, Agent, or Firm* — Condo Roccia Koptiw LLP

(57) ABSTRACT

Sensor-enabled surgical retractor devices, systems, and methods are disclosed herein that can be coupled to a surgical robot during a robotic or robot-assisted surgical procedure to maintain health of retracted anatomy and prolong the amount of time until a surgical procedure must be interrupted to adjust a retractor. In some embodiments, interruption of a surgical procedure can be avoided by providing for minor and, in some cases, automatically administered, adjustment of retractor devices to alleviate pressure on retracted tissue without requiring surgeon attention or intervention. Fine (e.g., minor) adjustments to the retractor can be made automatically over the course of a surgical procedure to prevent damage to retracted anatomy and increase the time until a major adjustment of the retractor is needed.

20 Claims, 6 Drawing Sheets

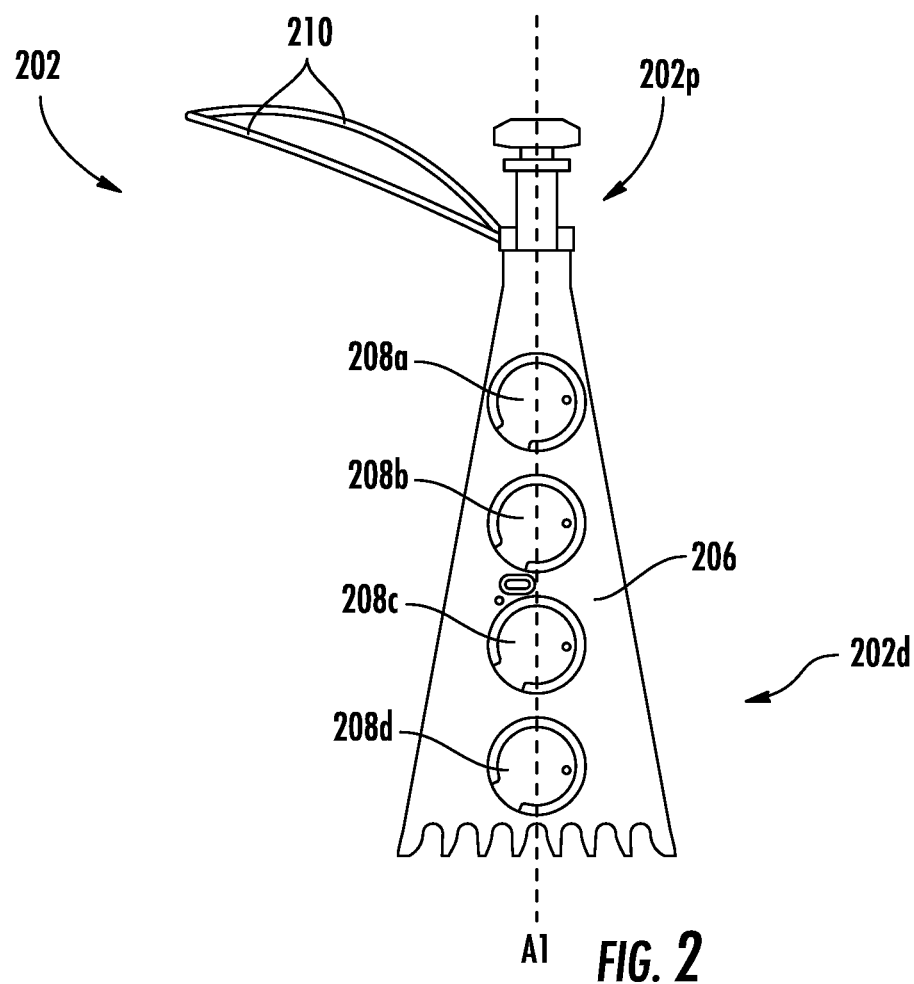
FIG. 2
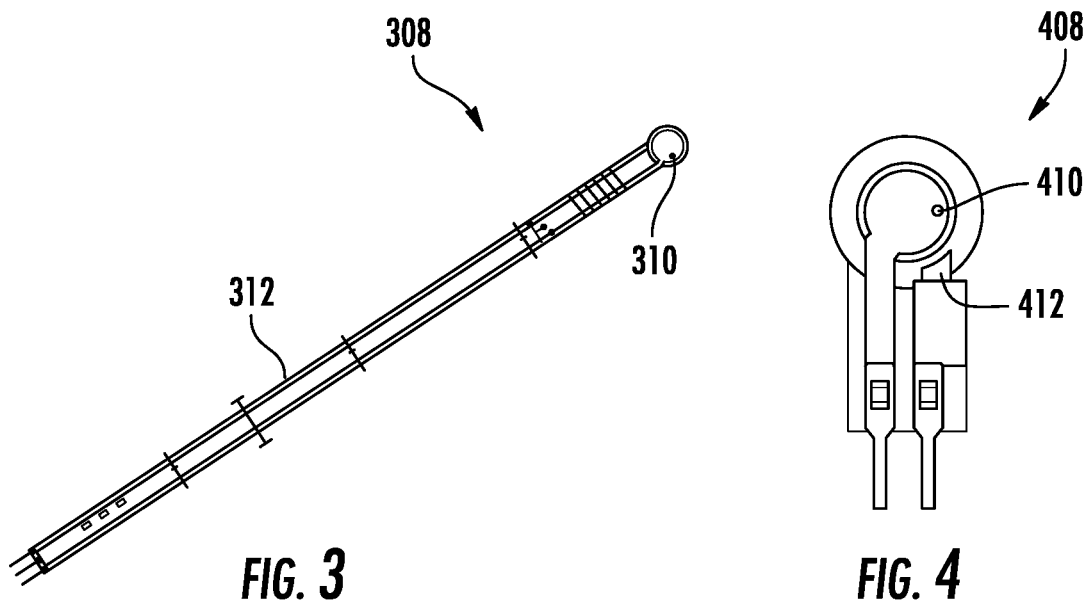
FIG. 3
FIG. 4

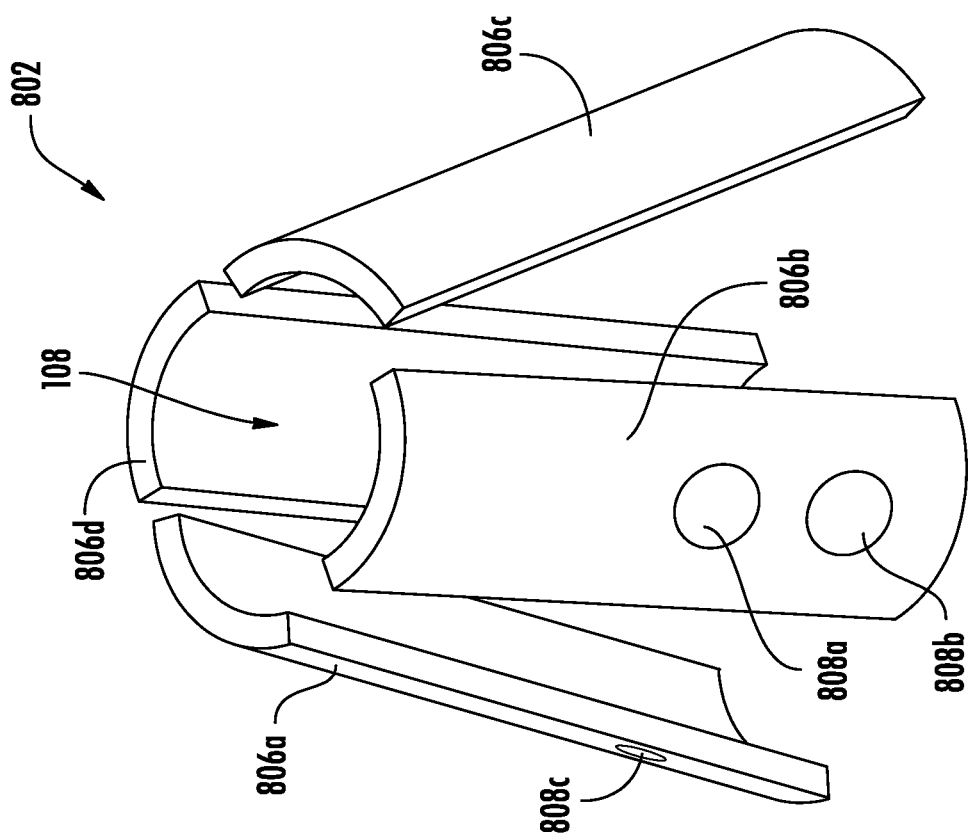
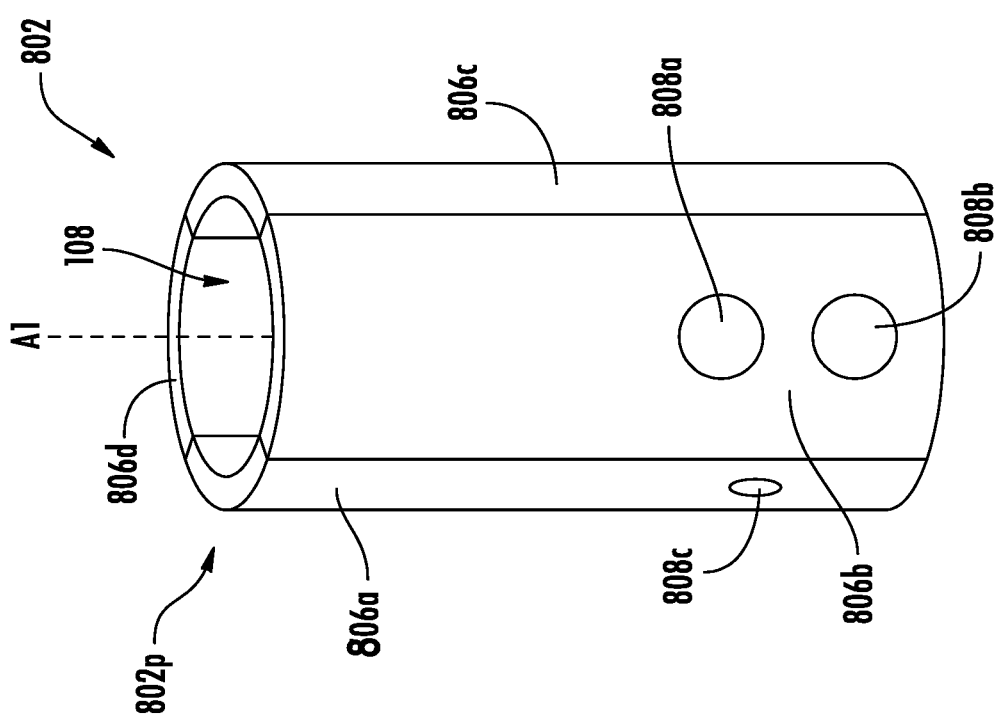

SENSOR ENABLED RETRACTOR FOR ROBOTIC SURGERY

CROSS-REFERENCE TO RELATED APPLICATIONS

This application claims priority to U.S. Provisional Application Ser. No. 63/051,863, filed on Jul. 14, 2020, the entire disclosure of which is hereby incorporated by reference.

BACKGROUND

Many surgical procedures require accessing a working area or surgical site within a patient via an access device, such as a cannula, retractor, or the like. Surgical instruments, implants, or other objects can be passed through a working channel of the access device and into the surgical site. The access device can retract nerves, blood vessels, ducts, or other anatomical structures that, in some instances, can be disposed in the path of the access device and can otherwise obstruct the working channel or require significant skill and dexterity to work around when performing surgery through the access device.

Retraction of tissue or other patient anatomy can cause fatigue and/or damage to the retracted anatomy due to an extended force applied by the retractor. Accordingly, over the course of a surgical procedure, a retractor or other access device can require repositioning to, for example, avoid tissue damage or necrosis. Known retractor repositioning techniques can involve manual or major adjustment of the retractor and can interrupt the flow of surgery, reduce surgical efficiency, extend the length of the overall surgical procedure, and increase risk to patient health/safety due to, for example, additional maneuvering of surgical instruments at the surgical site and the prolonged procedure.

Accordingly, there is a need for improved systems, methods, and devices for retracting patient anatomy to provide access to a surgical site in a manner that can improve patient outcome and surgical efficiency.

SUMMARY

Systems, methods, and devices are disclosed for surgical retraction, e.g., for retracting a portion of an anatomy of a patient at a surgical site ("retracted anatomy"), such as, for example, tissue (e.g., connective tissue, epithelial tissue, muscle tissue, and/or nervous tissue), to provide access to a surgical site in a robotic or robot-assisted surgical procedure. Sensor-enabled surgical retractor devices, along with related systems and methods, are disclosed herein that can be coupled to a surgical robot during a robotic or robot-assisted surgical procedure to maintain health of retracted anatomy and prolong the amount of time until a surgical procedure must be interrupted to adjust (e.g., majorly adjust) a retractor. In some embodiments, interruption of a surgical procedure can be avoided by providing for minor and, in some cases, automatically administered, adjustment of retractor devices to alleviate pressure on retracted tissue without requiring surgeon attention or intervention. Surgical systems of the present disclosure can include a retractor with one or more associated sensors (also referred to herein as a "sensor-enabled retractor"), a surgical robot arm, and a controller.

A variety of sensors can be utilized with the retractor, for example, to determine a parameter relating to the retracted anatomy. Examples of sensors include a force sensor to measure force experienced by retracted anatomy, a pressure sensor to measure pressure experienced by retracted anatomy, an optical sensor (such as, for example, a PPG sensor) to measure blood flow and blood oxygenation of retracted anatomy, a strain gauge which can measure retractor deflection for a pressure and/or force calculation, a torque sensor, a temperature sensor to measure local temperature and/or temperature variations, an ultrasound sensor that can measure changes in anatomical structures (e.g., such as nerves), and a neuromonitoring sensor that can measure nerve health in the retracted anatomy. Combinations thereof are contemplated, for example, in some embodiments, two or more types of associated sensors are employed. The sensors can gather data on one or more parameters relating to at least one of tissue (or other retracted anatomy) at the surgical site. Examples of parameters relating to retracted anatomy include a force exerted on retracted anatomy, a length of time at or above a certain (e.g., predefined) force, a pressure exerted on retracted anatomy, a length of time at or above a certain (e.g., predefined) pressure, blood flow of retracted anatomy, blood oxygenation of retracted anatomy, local temperature and/or temperature variations in retracted anatomy, changes in anatomical structures, and nerve health, and/or combinations thereof.

A controller can receive data from the sensor(s), monitor the one or more parameters to assess a status of the retracted anatomy. The controller can be configured to determine a parameter related to a placement of the retractor. Based on the parameter relating to the status of the retracted anatomy, the controller can determine to output one or more commands to the retractor and/or robot arm to change placement of the retractor, such as, at least one of a three-dimensional position (e.g., depth, latitude, etc.), configuration (e.g., open or closed), rotation, or angulation (e.g., with respect to an initial axis) of the retractor to maintain or improve health of the retracted anatomy without interruption to a surgical procedure being performed. In some embodiments, the command output by the controller can cause adjustment of the retractor position to maintain or improve the measured stress on a nerve. In this manner, fine (e.g., minor) adjustments to the retractor can be made automatically over the course of a surgical procedure to prevent damage to retracted anatomy and increase the time until a major adjustment of the retractor is needed. In some embodiments, a pressure sensor is associated with the retractor to measure stress on a nerve, such as a pressure sensor array extending along a length of the retractor.

In some embodiments, the controller can receive data from the sensor, monitor the one or more parameters to assess a status of the retracted anatomy, and output one or more commands to the retractor to cause an output of energy (e.g., one or more of vibrations, thermal energy, and electrical stimulations from the retractor to tissue in contact with the retractor) from the retractor to maintain or improve the tissue health (e.g., nerve health) at the surgical site.

In some embodiments, the controller can receive data from the sensor, monitor the one or more parameters to assess a status of the retracted anatomy, and output an alert to a user (e.g., surgeon) when nerve health at the surgical site is deteriorating based on the data gathered from the sensor.

Any of the features or variations described above or herein can be applied to any particular aspect or embodiment of the present disclosure in a number of different combinations.

BRIEF DESCRIPTION OF THE DRAWINGS

FIG. 2 depicts a sensor-enabled retractor;

FIG. 3 depicts a sensor for a sensor-enabled retractor;

FIG. 4 depicts a sensor for a sensor-enabled retractor;

FIG. 8A depicts a multi-blade sensor-enabled retractor in a closed configuration;

FIG. 8B depicts the retractor of FIG. 8A in an open configuration;

DETAILED DESCRIPTION

Figure 1:
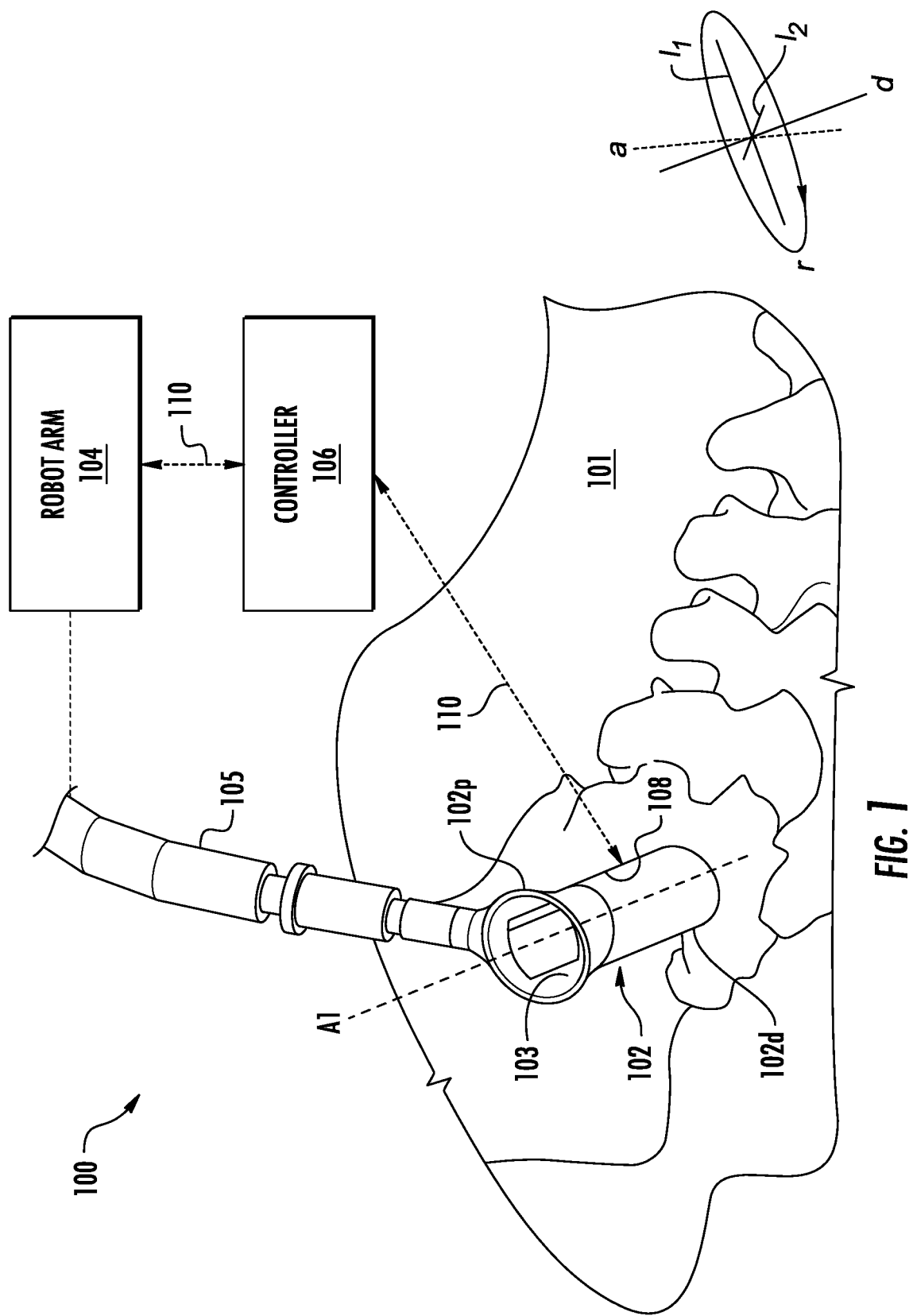
FIG. 1 depicts a schematic view of a surgical system according to the present disclosure.

Sensor-enabled surgical retractor devices, along with related systems and methods, are disclosed herein that can be coupled to a surgical robot during a robotic or robot-assisted surgical procedure to maintain health of retracted anatomy and prolong (or avoid) the amount of time until a surgical procedure must be interrupted to adjust a retractor. In some embodiments, interruption of a surgical procedure can be avoided by providing for minor and, in some cases, automatically administered, adjustment of retractor devices to alleviate pressure on retracted tissue without requiring surgeon attention or intervention. Surgical systems of the present disclosure can include a retractor with one or more associated sensors (also referred to herein as a "sensor-enabled retractor"), a surgical robot arm, and a controller. The retractor sensors can gather data on one or more parameters relating to at least one of tissue, or other patient anatomy, at the surgical site ("retracted anatomy"). For example, retracted tissue (e.g., connective tissue, epithelial tissue, muscle tissue, and/or nervous tissue) is an example of retracted anatomy. In some embodiments, the retracted anatomy comprises a nerve. The controller can receive data from the sensors, monitor the one or more parameters to assess a status of the retracted anatomy (e.g., at the surgical site), and output one or more command to the retractor and/or robot arm to maintain or improve health of the retracted anatomy without interruption to a surgical procedure being performed. In this manner, fine (e.g., minor) adjustments to the retractor can be made automatically over the course of a surgical procedure to prevent damage to retracted anatomy and increase the time until a major adjustment of the retractor is needed.

As used herein, fine (e.g., minor) adjustments are those adjustments to the retractor that do not result in a significant interruption of the surgical procedure. Examples of significant interruptions include blocking access to the surgical site or working channel or requiring removal of a surgical instrument. In contrast, the systems, methods, and devices disclosed herein can make fine (e.g., minor) adjustments to the retractor to maintain and/or improve health of the retracted anatomy without significantly interrupting the surgical procedure. In some embodiments, the adjustments can be automatic (e.g., via a closed loop). As described in detail below, such fine (e.g., minor) adjustments to the retractor can include one or more of changes to a placement of the retractor, such as narrowing or slightly closing the retractor temporarily, such narrowing can be accomplished considering the current trajectory of an instrument such that a particular retractor blade can be slightly moved towards the closed position such that the instrument currently in the retracted space is not interfered with (or a signal to the surgeon to adjust a particular retractor blade manually), or output of energy from the retractor (e.g., one or more of vibrations, thermal energy, and electrical stimulations from the retractor to tissue in contact with the retractor) of at least part of the retractor. The systems, methods, and devices disclosed herein can be configured to go back to an original configuration of retractor after predefined time, or upon a time based on a measured value/time that the measure value is above a certain (e.g., predefined) threshold. In some embodiments, the number of fine (e.g., minor) adjustments can be limited to a certain (e.g., predefined) number of automatic minor adjustments, and after exceeding that number, a warning (e.g., to the surgeon) is generated. Accordingly, the systems, methods, and devices disclosed herein can extend a time period during which a surgical procedure can be performed continuously without interruption for a manual or a major adjustment of a retractor, which can improve patient outcome and surgical efficiency.

Some embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment can be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. Equivalents to such linear and circular dimensions can be determined for different geometric shapes. Further, in the present disclosure, like-numbered components of the embodiments generally have similar features. Still further, sizes and shapes of the devices, and the components thereof, including, for example, a size and shape of a sensor-enabled retractor, can depend at least on the anatomy of the subject in which the devices will be used, the size and shape of objects with which the devices will be used, and the methods and procedures in which the devices will be used.

FIG. 1 illustrates one embodiment of a surgical system 100 of the present disclosure for use upon a patient 101 that can include a sensor-enabled retractor 102 disposed within an incision to create a working channel 103 to access a surgical site within the patient, a surgical robot arm 104, and a controller 106. While the schematic of FIG. 1 illustrates a tubular retractor, any of a variety of retractor designs are possible, including single or multi-bladed retractors, etc., as will be described. A proximal end 102p of the retractor 102 can be coupled to the robot arm 104, for example, via an articulating distal portion 105 of the robot arm. The robot arm 104, upon receiving commands from the controller 106, can control, among other things, a three-dimensional position (e.g., depth or latitude), a rotation, and an axial orientation ("angulation") of the retractor 102. A distal end 102d of the retractor 102 can be inserted through the incision in the patient towards the surgical site to create or clear the working channel 103 for access to the surgical site. More particularly, an outer surface of the retractor 102, e.g., a surface facing away from the working channel 103, can contact patient anatomy, such as tissue, including nervous tissue ("nerve" or "nerves") etc., and can retract the anatomy away from the working channel and surgical site. The working channel 103 can extend along a longitudinal axis A1 and can provide access to the surgical site. The retractor 102 can have one or more sensors 108 associated with the retractor, in the presently described embodiment, disposed on the outer surface of the retractor. The sensor 108 can gather data, including one or more of a parameter related to a patient's retracted anatomy, for example, a parameter related to a patient tissue at the surgical site. Examples of sensors will be described, however, it is understood that such sensors can monitor a force applied by the retractor 102 to the retracted anatomy, pressure exerted on the retracted anatomy, blood oxygenation of the retracted anatomy, blood flow in the retracted anatomy, temperature, retractor deflection for a pressure and/or force calculation, a torque, changes in anatomical structures, such as nerves, and nerve health. The sensor 108 can communicate with the controller 106 (and the controller can communicate with the robot arm 104) via communication paths 110, which can be physical signal transmission paths (e.g., wires) or a wireless connection as will be described. The controller 106 can determine a parameter related to the retractor, for example, a current three-dimensional position, configuration (in tubular retractors, the configuration can be considered as unchanging), rotation (in tubular retractors, the rotation can be considered as unchanging), or angulation (e.g., with respect to axis A1) of the retractor. As can be appreciated, in symmetrical tubular reactors, one or more of the configuration and rotation can be considered as unchanging). The controller 106 can be operatively coupled to at least one of the retractor 102 and the robot arm 104 and can, among other things, receive data from the retractor sensor(s) and output one or more commands to the retractor and/or robot arm based, at least in part, on the sensor data to cause fine (e.g., minor) adjustment of the retractor to maintain or improve health of the retracted anatomy (e.g., without requiring a major adjustment).

By way of example, the controller can send commands which result in the robot arm 104 moving and thereby changing one or more of an angle a of the retractor 102 with respect to the axis A1, a depth d of the retractor in the patient along the axis A1, a rotation r around the axis A1, a first lateral position $l_1$ in the patient corresponding to a lateral displacement from the axis A1, and a second lateral position $l_2$ in the patient corresponding to changing one or more of a diameter of the working channel 108. Such movement can maintain or improve health of the retracted anatomy without interruption to a surgical procedure being performed. For example, such movement can be beneficial in order to reduce stress on a nerve. The controller can determine the movement that best maintains or improves health of the retracted anatomy. The controller can send commands which result in the retractor producing an output of the retractor (e.g., one or more of vibrations, thermal energy, and electrical stimulations from the retractor to tissue in contact with the retractor). The controller 106 can be configured to receive data from the sensor 108 via one or more of the communication paths 110, monitor one or more parameters to assess a status of the retracted anatomy, and output an alert to a user (e.g., surgeon) when nerve health at the surgical site is deteriorating based on the data gathered from the sensor.

FIG. 2 illustrates a sensor-enabled blade retractor 202 that can be used in the surgical system 100 of FIG. 1. The illustrated retractor 202 can be a single blade retractor or a multi-blade sensor-enabled retractor. The retractor 202 can have a proximal end 202p that can be operatively coupled to the robot arm 104. A distal portion 202d of the retractor 202 including a blade 206, can be inserted through an incision in a patient towards a surgical site to retract tissue away from a working channel. In the embodiment illustrated in FIG. 2, the retractor blade 206 can be generally planar with a triangular shape, however a retractor blade having a different geometric configuration is within the scope of the present disclosure.

One or more sensors 208a, 208b, 208c, 208d can be coupled to the retractor blade 206 and can gather data including one or more of a parameter related to tissue at the surgical site adjacent to the retractor. For example, the sensors 208a, 208b, 208c, 208d can be force sensors that can detect a force exerted by the retractor 202 onto tissue retracted by the retractor. In the illustrated embodiment, the force sensors 208a, 208b, 208c, 208d can be substantially aligned along a longitudinal axis A1 of the retractor. A number and/or placement of the force sensors 208a, 208b, 208c, 208d can be varied based on, for example, the geometry of a particular retractor and/or the particular intended use of the retractor. As discussed in detail below, the data gathered by the sensors 208a, 208b, 208c, 208d can be transmitted to the controller 106 and can be used to assess and monitor health of the retracted anatomy.

The sensors 208a, 208b, 208c, 208d can be fully integrated into or embedded within the retractor 202. For example, any circuitry or wiring required for operation of the sensors 208a, 208b, 208c, 208d can extend through an interior of the retractor 202. In some embodiments, the sensors 208a, 208b, 208c, 208d can communicate with a robot arm and/or a controller through a physical signal transmission path, such as wires 210, that can extend from the proximal end 202p of the retractor 202 to communicatively and operably couple the retractor and associated sensors to the robot arm and/or controller. Additionally, or alternatively, the sensors 208a, 208b, 208c, 208d can wirelessly communicate with the robot arm and/or controller, e.g., through near-field communication (NFC), WIFI™, BLUETOOTH™, BLUETOOTH LE™, ZIGBEE™, etc. In the case of a wireless communication, a communication protocol can be selected to provide a desired communication range. For example, in some embodiments, BLUETOOTH™ (e.g., class 2 BLUETOOTH™ having a range of 5-10 meters) can be used to allow the retractor 202 to remain somewhat distant from the controller while at the same time limiting the communication range such that other devices unlikely to be used in the surgery are not needlessly involved. Regardless of whether the communication is wired or wireless, the sensors 208a, 208b, 208c, 208d can transmit gathered data on one or more parameters, e.g., the force exerted by the retractor on the retracted tissue, to the controller.

Other sensors and alignments are contemplated. FIG. 3 shows a force sensor 308 that can have a force sensing area 310 with circuitry 312 extending therefrom. In some embodiments, the sensing area 310 can be circular with a diameter of about 9.53 mm. The circuitry 312 can extend from the sensing area 310 such that the force sensor 308 can have a length of up to about 191 mm. A length of the circuitry 312 can be adjusted, e.g., trimmed, to a desired length such that the sensor 308 can be integrated into a retractor blade (such as, for example, blade 206 of FIG. 2) with the sensing area 310 placed at a desired position.

FIG. 4 shows a force sensor 408 that can have a smaller sensing area 410 as compared to the sensing area 310 of FIG. 3. For example, the sensing area 410 of the sensor 408 can be circular with a diameter of about 3.8 mm. Circuitry 412 can extend from the sensing area 410 such that an entire length of the force sensor 408 can be about 15.6 mm. The recited dimensions provide non-limiting examples of sensors that can be used with sensor-enabled retractors of the present disclosure. Sensors of differing sizes can be utilized depending on the type of surgical procedure (e.g., minimally invasive surgery vs. open surgery, etc.), a particular area of anatomy being accessed, etc.

Figure 5:
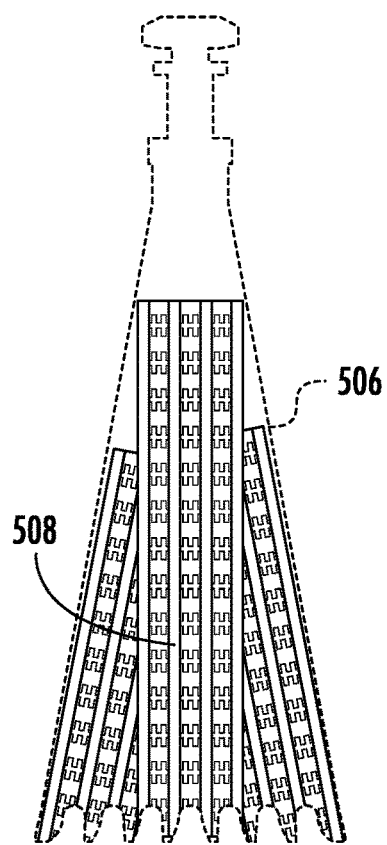
FIG. 5 depicts a sensor for a sensor-enabled retractor.

FIG. 5 illustrates a pressure sensor 508 that can be coupled to the retractor blade 506, for example, as part of a sensor-enabled retractor that is a variation of the retractor 202 of FIG. 2. The sensor 508 can comprise an integrated pressure array that can detect pressure of patient anatomy in contact with the retractor, e.g., retracted tissue, across a surface area of the pressure array. In some embodiments, the array of the sensor 508 can extend across substantially an entire surface of the blade 506. In this manner, the array of the sensor 508 can gather data on substantially an entire area of tissue, or other retracted anatomy, in contact with the blade 506. Data gathered from the pressure array of the sensor 508 can be used by a controller to, among other things, identify a location of peak pressure in the retracted anatomy, compare the location of peak pressure to a location of nerves in the retracted anatomy, map tissue pressure onto nerve locations, determine nerve health, etc. A geometric configuration of the array of the sensor 508 can be adapted based, at least in part, on either a shape of the retractor to be coupled to or an intended use, e.g., a particular surgical procedure or anatomy to be retracted.

Sensor-enabled retractors of the present disclosure can include multi-modality sensors for gathering data (e.g., overlapping data or independent data) related to the retracted anatomy. For example, different sensors on the same retractor can measure a same parameter. Alternatively, different sensors on the same retractor can measure different parameters. Examples of parameters include monitor a force applied by the retractor to the retracted anatomy, a pressure exerted on the retracted anatomy, blood oxygenation of the retracted anatomy, blood flow in the retracted anatomy, temperature, changes in anatomical structure, and/or nerve health.

Figure 6:
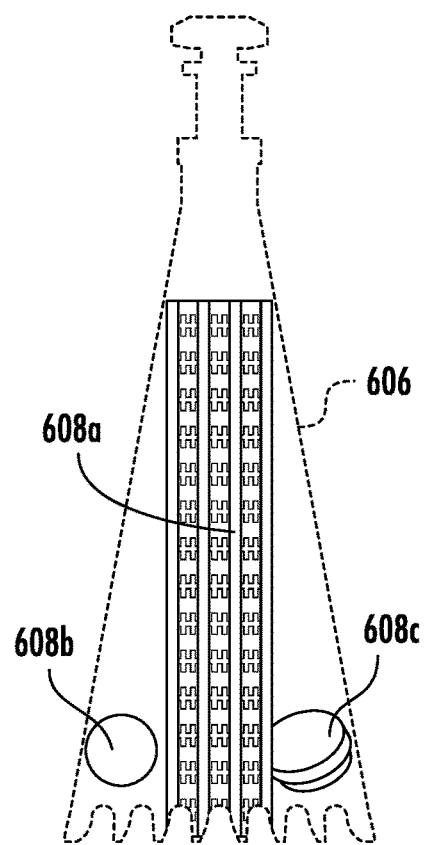
FIG. 6 depicts a sensor for a sensor-enabled retractor.

FIG. 6 illustrates a plurality of sensors 608a, 608b, 608c, each of which can represent a different sensing technology or modality, the sensors being coupled to a retractor blade 606, for example, as part of a sensor-enabled retractor. The retractor blade 606 can retract the retracted anatomy away from a working channel and/or surgical site. The retractor blade 606 can include a pressure array sensor 608a, an optical sensor (such as, for example, a photoplethysmography (PPG) sensor) 608b, and a temperature sensor 608c, each of which can gather data from the retracted tissue. More particularly, the pressure array sensor 608a can extend longitudinally along substantially an entire length of the retractor blade 606 and can gather pressure data from tissue in contact with the retractor, e.g., can gather data on substantially an entire area of tissue, or other retracted anatomy, in contact with the blade. Data gathered from the pressure array sensor 608 can be used by a controller to, among other things, identify a location of peak pressure in the retracted anatomy, compare the location of peak pressure to a location of nerves in the retracted anatomy, map tissue pressure onto nerve locations, determine nerve health, etc. The optical sensor 608b and the temperature sensor 608c can each be coupled to the retractor blade 606 towards a distal end. The optical sensor 608b can measure blood oxygenation and blood flow of retracted tissue. In some embodiments, the optical sensor 608b can be located on the retractor blade 606 such that the sensor 608b can be aligned with a particular area of nerves in the retracted anatomy. The temperature sensor 608c can measure a temperature of the retracted tissue. In the illustrated embodiment, the pressure array sensor 608a can be centrally located, with the optical sensor 608b and the temperature sensor 608c coupled to the retractor blade on the either side of the pressure array. Alternative placement of the sensors 608a, 608b, 608c relative to the retractor blade 606 or one another is within the scope of this disclosure. Moreover, the sensor-enabled retractor can have a plurality of the same sensing technologies or modalities, if desired. Each of the sensors 608a, 608b, 608c can transmit data to a controller and can independently be connected to the controller via a wired connection or wirelessly.

Sensor-enabled retractors of the present disclosure can include a variation on the number, locations, and/or types of sensors that can be coupled to the retractor to gather data on tissue, or other patient anatomy, retracted by the retractor. By way of non-limiting example, sensor-enabled retractors of the present disclosure can include one or more of the following sensors coupled to a retractor blade or body: a force sensor to measure force exerted on retracted anatomy, a pressure array to measure pressure of retracted anatomy, an optical sensor (such as, for example, a PPG sensor) to measure blood flow and blood oxygenation of retracted anatomy, a strain gauge which can measure retractor deflection for a pressure and/or force calculation, a torque sensor, a temperature sensor to measure local temperature and/or temperature variations, an ultrasound sensor that can measure changes in anatomical structures, such as nerves, a neuromonitoring sensor that can measure nerve health in the retracted anatomy, such as a SENTIOMMG™ smart sensor.

Figure 7:
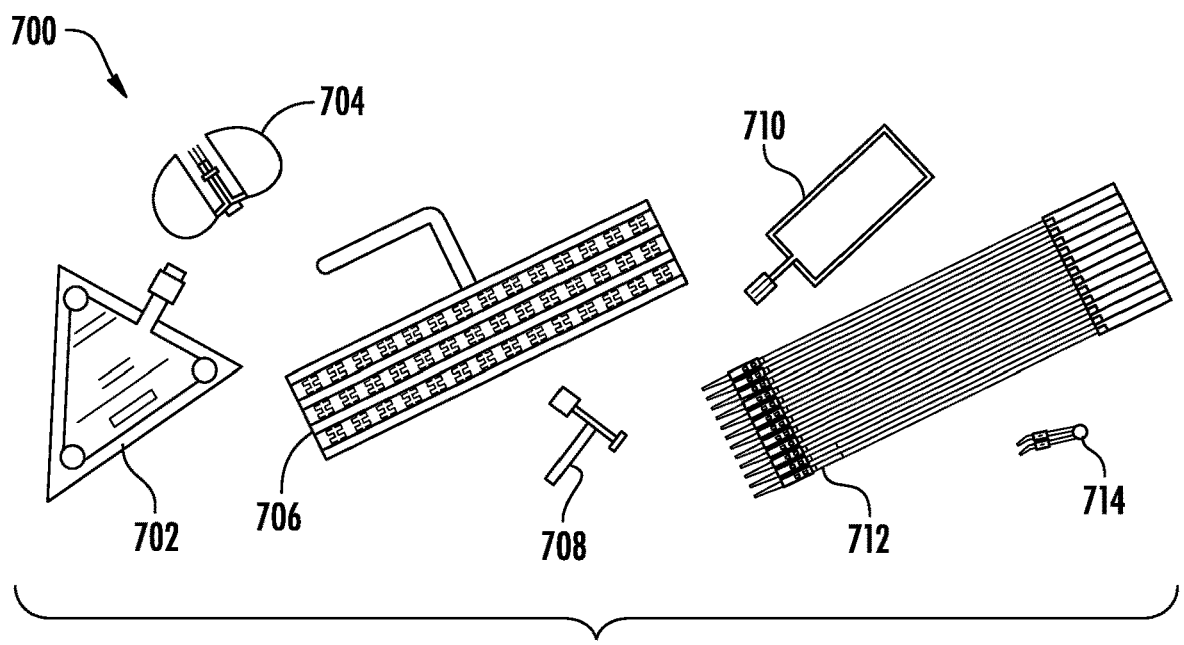
FIG. 7 depicts a kit containing a plurality of sensors that can be integrated with a sensor-enabled retractor.

In some embodiments, a sensor-enabled retractor of the present disclosure can include a custom sensor matrix that can be selected (e.g., for example by the surgeon) from a kit of sensors of varying, sizes, shapes, modalities, etc. to be affixed to a retractor. FIG. 7 illustrates one embodiment of a sensor kit 700 that can include pressure sensors of varying sizes and shapes 702-714 and can be used to create a custom pressure sensor matrix for a sensor-enabled retractor.

FIGS. 8A and 8B show one embodiment of a sensor-enabled tube-shaped blade retractor 802 with a plurality of retractor blades 806a, 806b, 806c, and 806d. While the retractor 802 is shown with four retractor blades, it is understood that the number of blades of a multi-blade retractor can be greater or fewer than four. A proximal end 802p of the retractor can be coupled to a robot arm. FIG. 8A shows the retractor 802 in a closed configuration in which the retractor blades 806a-d can enclose or substantially enclose the working channel 803 that can extend through the retractor 802. One or more of the retractor blades 806a-d can include one or more of the sensors described above to measure a parameter relating to at least one of tissue at the surgical site or the retractor. By way of non-limiting example, one retractor blade 806b can include a first force sensor 808a and a second force sensor 808b that can measure a force exerted on tissue retracted by the retractor 802. Another retractor blade 806a of the retractor 802 can include a different type of sensor, such as an optical sensor 808c. In other embodiments, one or more of the retractor blades can include a combination of one or more of the above-mentioned sensors such that multiple sensors are disposed on one or more of the retractor blades.

FIG. 8B shows the retractor 802 in an open configuration, in which one or more of the retractor blades 806a-d can be moved radially outward from the longitudinal axis A1 of the working channel 803 to retract patient anatomy and open the working channel. In some embodiments, the robot arm can move one or more of the retractor blades 806a-d, either simultaneously or sequentially, to open the working channel. As discussed in detail below, the controller can output one or more commands to the robot arm to make a fine (e.g., minor) adjustment to one or more of the retractor blades 806a-d in response to data gathered by the one or more sensors 808a-c. For example, one or more of the following fine (e.g., minor) adjustments can be made to one or more of the blades 806a-d: the blade(s) can be rotated circumferentially about the working channel 803; a deflection of the blade(s) can be adjusted by pivoting the blade(s) relative to the longitudinal axis A1 of the working channel; a lateral retraction of the blade(s) can be adjusted by opening or closing the blade(s) radially with respect to the longitudinal axis of the working channel. In some embodiments, a fine (e.g., minor) adjustment can be made in any of the foregoing directions, or a change to the axis A1 can be made.

Figure 9:
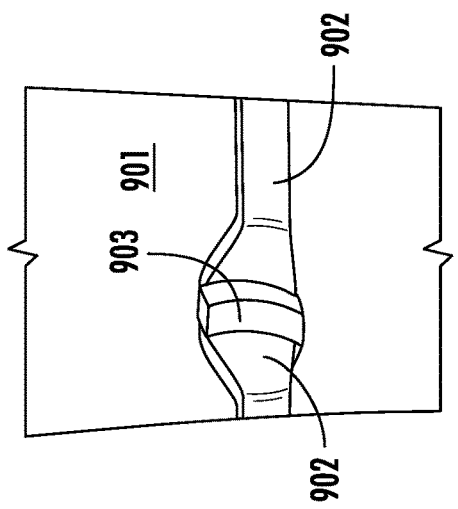
FIG. 9 depicts a multi-blade sensor-enabled retractor retracting tissue in a patient.

In use, the present surgical retractor system is compatible with a number of retractor types and sensor types. FIG. 9 illustrates a sensor-enabled retractor 902 of the present disclosure forming a working channel 903 in a patient 901. The retractor 902 can have a pair of opposing retractor blades. One or more of the retractor blades can include one or more of the sensors described herein (e.g., a force sensor to measure force experienced by retracted anatomy, a pressure sensor to measure pressure experienced by retracted anatomy, an optical sensor (such as, for example, a PPG sensor) to measure blood flow and blood oxygenation of retracted anatomy, a strain gauge which can measure retractor deflection for a pressure and/or force calculation, a torque sensor, a temperature sensor to measure local temperature and/or temperature variations, an ultrasound sensor that can measure changes in anatomical structures, such as nerves, and a neuromonitoring sensor that can measure nerve health in the retracted anatomy) that can gather data pertaining to retracted anatomy. A proximal end of the retractor 902 can be coupled to a robot arm. In some embodiments, each of the retractor blades can be similar or identical to any one of the retractor blades described above. The retractor blades can be moved laterally to retract patient anatomy and open the working channel 903 formed between the blades. Further, the robot arm 1 can make fine (e.g., minor) adjustments, as described above, to one or more of the blades in response to commands from the controller based on the retracted tissue parameters based on sensor data, which can extend the amount of time a surgical procedure can be performed continuously prior to requiring a major or manual adjustment of the retractor 902.

Figure 10:
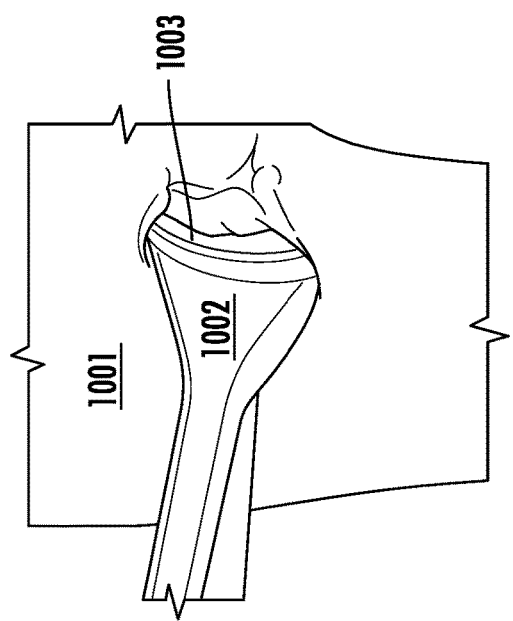
FIG. 10 depicts a single-blade sensor-enabled retractor retracting tissue in a patient.

FIG. 10 shows a sensor-enabled retractor 1002 with a single blade inserted through an incision into a patient 1001 to create a working channel 1003. The retractor 1002 can include one or more of the sensors described herein (e.g., a force sensor to measure force experienced by retracted anatomy, a pressure sensor to measure pressure experienced by retracted anatomy, an optical sensor (such as, for example, a PPG sensor) to measure blood flow and blood oxygenation of retracted anatomy, a strain gauge which can measure retractor deflection for a pressure and/or force calculation, a torque sensor, a temperature sensor to measure local temperature and/or temperature variations, an ultrasound sensor that can measure changes in anatomical structures, such as nerves, and a neuromonitoring sensor that can measure nerve health in the retracted anatomy) that can gather data pertaining to retracted patient anatomy. A proximal end of the retractor 1002 can be coupled to the robot arm. Further, the robot arm can make fine (e.g., minor) adjustments, as described above, in response to commands from the controller based on the retracted tissue parameters based on sensor data, which can extend the amount of time a surgical procedure can be performed continuously prior to requiring a major or manual adjustment of the retractor 1002.

Figure 11:
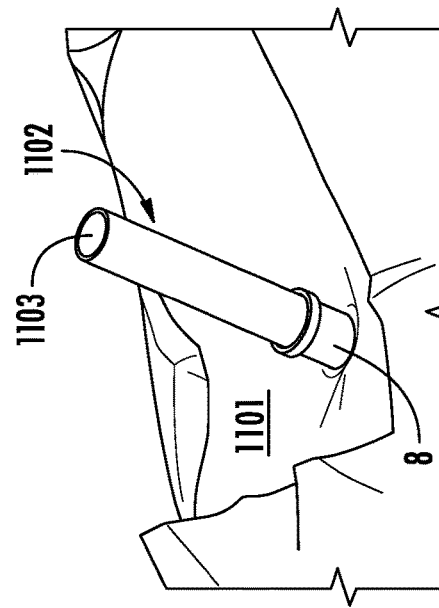
FIG. 11 depicts a tubular sensor-enabled retractor retracting tissue in a patient.

FIG. 11 illustrates another embodiment of a sensor-enabled retractor 1102 of the present disclosure having a tubular retractor body, e.g., a tubular access port. A distal portion of the retractor 1102 can be inserted through an incision in a patient 1101 with the working channel 1103 extending through the retractor 1102, e.g., through an inner lumen of the tubular access port. The distal portion can include one or more sensors described herein (e.g., a force sensor to measure force experienced by retracted anatomy, a pressure sensor to measure pressure experienced by retracted anatomy, an optical sensor (such as, for example, a PPG sensor) to measure blood flow and blood oxygenation of retracted anatomy, a strain gauge which can measure retractor deflection for a pressure and/or force calculation, a torque sensor, a temperature sensor to measure local temperature and/or temperature variations, an ultrasound sensor that can measure changes in anatomical structures, such as nerves, and a neuromonitoring sensor that can measure nerve health in the retracted anatomy) to measure one or more parameters related to one or more of tissue at the surgical site. For example, in some embodiments, a pressure array sensor can extend along at least a portion of retractor 1102 and can measure pressure of tissue in contact with an outer surface of the retractor. The one or more sensors associated with the retractor 1102 can transmit data pertaining to retracted tissue to the controller. In response to commands from the controller based on the parameters, the robot arm can make fine (e.g., minor) adjustments, as described above, which can extend the amount of time a surgical procedure can be performed continuously prior to requiring a major or manual adjustment of the retractor 1102.

Figure 12:
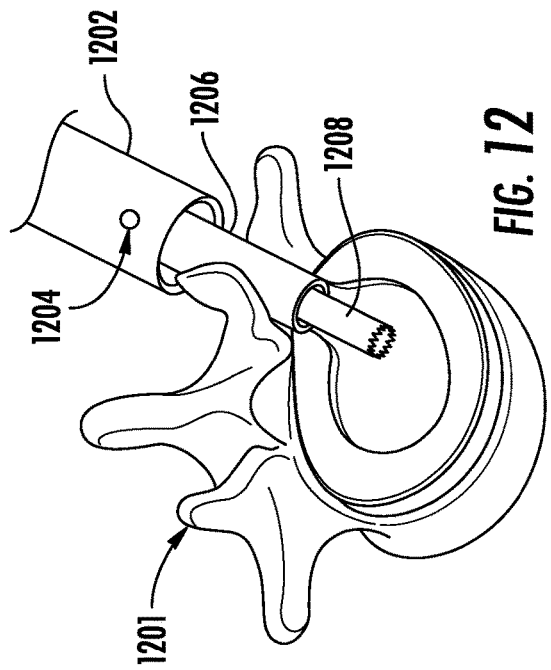
FIG. 12 depicts a tube-in-tube sensor-enabled retractor retracting tissue in a patient.

FIG. 12 illustrates still another embodiment of a sensor-enabled retractor 1202 having a tube-in-tube configuration with an inner shield 1206 (also shown is a representative surgical tool, such as a disc removal tool 1208). A pressure sensor 1204 is disposed upon the retractor 1202 to measure the stress on an adjacent nerve (not depicted) of the patient anatomy 1201. Moreover, a second modality of sensing is provided by using ultrasound techniques that can measure distance, e.g., the controller can measure the elongation of the nerve under retraction and define a maximum elongation limit (e.g., 20%), and then warn the surgeon if the elongation limit is exceeded. In some embodiments, the system can associate the ultrasound capabilities with the retractor 1202 and thereby navigate the retractor. More details on this type of configuration can be found in U.S. Ser. No. 15/254,877 (Pat. Pub. No. 2017/0065269, entitled "Multi-Shield Spinal Access System"), the entire contents of which are incorporated by reference herein in its entirety. When using such a system, if the ultrasound sensor notes high stress on the nerve, e.g., stress above a certain (e.g., predefined) threshold level for a certain (e.g., predefined) length of time, the controller can be configured to move the retractor 1202 (e.g., to relax the nerve). For example, the retractor 1202 could change its angulation, rotate, translate, etc., in order to reduce stress on the nerve.

Figure 13:
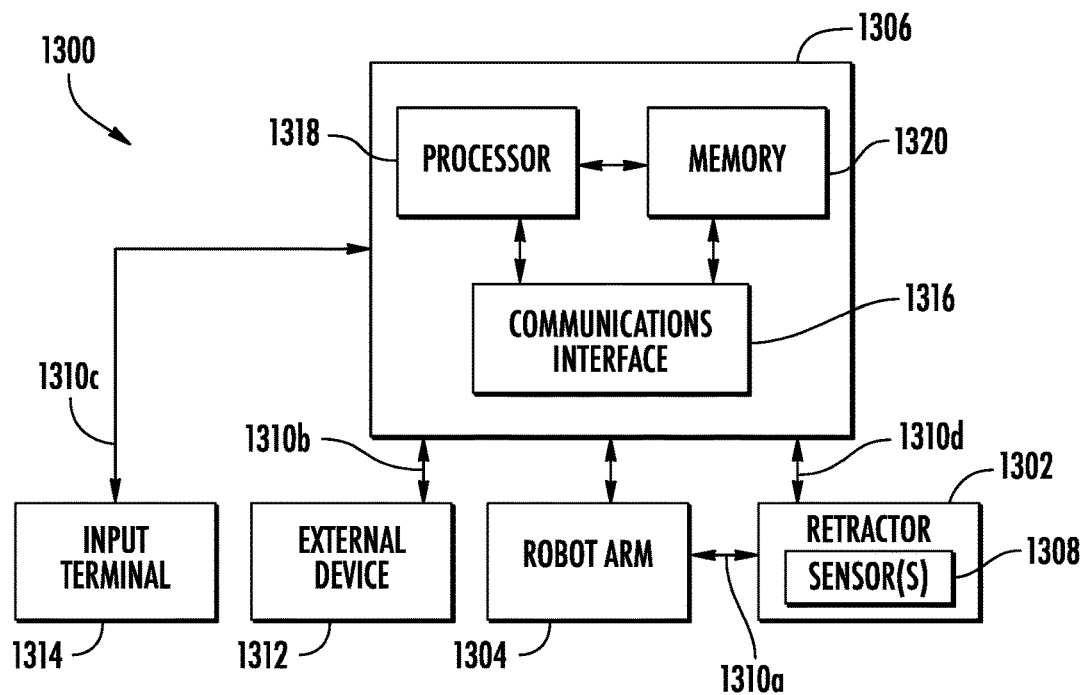
FIG. 13 is a block diagram of a surgical system according to the present disclosure.

FIG. 13 is a block diagram 1300 of a surgical retractor system. The system 1300 can include a retractor 1302, a robot arm 1304, and a controller 1306. The retractor 1302 can include one or more sensors 1308, such as any of the sensors described above, that can detect or gather data including at least one parameter related to retracted tissue. The retractor 1302 can be coupled to the robot arm 1304 such that a position, rotation, configuration, and/or angulation of the retractor 1302 can be controlled by the robot arm. The robot arm 1304 and the retractor 1302 are physically coupled, and can be communicatively coupled via a wired or wireless data transmission path 1310*a*. As described above, the controller 1306 is communicatively coupled via a wired or wireless data transmission path 1310*d* to the retractor 1302. As described above, the controller 1306 is communicatively coupled via a wired or wireless data transmission path to the robot arm 1304. In some embodiments, controller 1306 can be communicatively coupled via wired or wireless data transmission paths 1310*b*, 1310*c* to one or more external devices 1312 and/or input terminals 1314.

The controller 1306 can include a communications interface 1316, a processor 1318, and a memory 1320, each of which can be in communication with one another. Although each of these components are referred to in the singular, it will be appreciated that the various functions described as being carried out by one of the components can be carried out by multiple of these components, e.g., the functions described as being carried out by the processor 1318 can be carried out by multiple processors, etc.

The controller 1306 can transmit data to and receive data from the retractor 1302 and the robot arm 1304 via the communications interface 1316. As introduced above, in some embodiments, the controller 1306 can communicate with one or more external device 1312 and/or one or more input terminal 1314. By way of non-limiting example, the external device 1312 can be a display, a computing device, remote server, etc. The input terminal 1314 can be configured to allow a surgeon or other user to input data directly into the controller 1306. Such data can include patient information, surgical procedure information, and the like. The input terminal 1314 can be any known input device, for example, a keyboard and/or cursor. The communication interface 1316 can be wireless (e.g., near-field communication (NFC), WIFI™, BLUETOOTH™, BLUETOOTH LE™, ZIGBEE™, and the like) or wired (e.g., USB or Ethernet). In some embodiments the communication interface can include one or more wireless and wired connections. In the case of a wireless connection, the communication interface 1316 can be selected or programmed to provide a desired communication range. The communications interface 1316 can receive data from the one or more retractor sensors 1308 via the communication path 1310*d* (e.g., a physical signal transmission path or a wireless connection).

The sensors 1308 can transmit data gathered or sensed regarding the retracted anatomy (e.g., parameters) to the communications interface 1316. The data transmitted from the sensors 1308 can include, but is not limited to, one or more of a force applied to retracted anatomy, a pressure measurement of the retracted anatomy, a blood oxygenation measurement of the retracted anatomy, a blood flow measurement in the retracted anatomy, a temperature of the retracted anatomy, a retractor deflection for a pressure and/or force calculation, a retractor torque, and a measurement or ultrasound of nerve health, each of which can also be referred to as a parameter. The particular type of data transmitted to the controller 1306 will depend on the type of sensor(s) 1308 coupled to the retractor 1302. The communications interface 1316 can transmit the parameter data received from the retractor sensors 1308 to the memory 1320 for storage and/or to the processor 1318 for analysis.

The processor 1318 can include a microcontroller, a microcomputer, a programmable logic controller (PLC), a field-programmable gate array (FPGA), an application specific integrated circuit (ASIC), integrated circuits generally referred to in the art as a computer, and other programmable circuits, and these terms are used interchangeably herein. As noted above, the processor 1318 can be coupled to the communications interface 1316 and the memory 1320. The processor 1318 can use data received from the retractor sensors 1308 as inputs to monitor and assess health of retracted anatomy and can output one or more commands, via the communications interface 1316, to the retractor 1302 and/or robot arm 1304 to maintain or improve health of the retracted anatomy. As noted above, the commands can include fine (e.g., minor) adjustments of the retractor 1302 such that the surgical procedure can continue uninterrupted without damage to the anatomy.

For example, the controller 1306 can transmit one or more commands to the robot arm 1304 to make a fine (e.g., minor) adjustment to a position, configuration, rotation, or angulation of at least part of the retractor 1302, which can relieve pressure on retracted anatomy to prevent tissue damage, tissue necrosis, or nerve hibernation. For example, the controller 1306 can output a command to the robot arm 1304 for the robot arm to move the retractor 1302 to change the configuration of the retractor (open to closed), rotate at least a portion of the retractor (e.g., one or more retractor blade) circumferentially about a longitudinal axis of the working channel, change the angle of at least a portion of the retractor, or laterally move at least a portion of the retractor.

Additionally, or alternatively, the controller 1306 can transmit one or more commands to the retractor 1302 to maintain or improve health of retracted anatomy, e.g., to prevent tissue damage, tissue necrosis, or nerve hibernation. For example, in some embodiments, the controller 1306 can command the retractor 1302 to output one or more of physical vibrations, thermal energy, and electrical stimulation to tissue, or other retracted anatomy, in contact with the retractor. Physical vibrations or electrical stimulations can increase or stimulate blood flow through retracted tissue. The retractor 1302 can output thermal energy to heat tissue in contact with the retractor, which can increase blood flow in the tissue. Alternatively, the retractor 1302 can cool tissue in contact with the retractor, which can reduce inflammation of the tissue.

The system 1300 can operate as a closed-loop feedback system. More particularly, the retractor sensors 1308 can transmit data to the controller 1306 in real-time (e.g., at a rate approaching or faster than once every second, for example, at a rate of about once every 10 to 100 milliseconds) or at other regular programmable intervals, e.g., about every 15 seconds, about every 30 seconds, about every minute, etc. The processor 1318 can receive data from the retractor sensors 1308 and can assess the health of the retracted anatomy. Based on the health assessment of the retracted anatomy, one or more commands can be output to the retractor 1302 and/or robot arm 1304 in real-time or at other regular programmable intervals, e.g., about every 15 seconds, about every 30 seconds, about every minute, etc., to maintain or improve health of the retracted anatomy. Alternatively, the processor 1318 can be configured to output one or more command to the retractor 1302 and/or the robot arm 1304 in response to a predefined parameter or overall health of the retracted anatomy reaching a predefined threshold point. For example, the retractor sensors 1308 can include at least one neuromonitoring sensor that can monitor the health of retracted nerves, e.g., a nerve response time, maximum elongation limit, or amplitude to a stimulation from the sensor. This data can be transmitted to the controller 1306 and can be monitored over time. If a decay in the nerve health is detected, or decay beyond a certain (e.g., predefined) threshold is detected, or maximum elongation limit reached, the controller 1306 can output a command to the robot arm 1304 and/or retractor 1302 to make a minor adjustment to prevent damage to the nerve.

In some embodiments, the controller 1306 can alert a user (e.g., surgeon) when certain (e.g., predefined) thresholds pertaining to health of the retracted tissue are reached or surpassed. For example, a user can be alerted if a pressure of the retracted tissue exceeds a threshold amount. The alert can include illumination of an LED or other visual alert on the external device 1312 or other component of the system 1300, the triggering of an alarm sound, the logging of information in a connected server, external device, or computing system, etc. By way of further example, a user can be alerted when a time of retractor deflection exceeds a threshold, when a pressure applied over a given time exceeds a threshold, when nerve health is deteriorating, when nerve health deteriorates below a certain (e.g., predefined) threshold, when a maximum elongation limit of a nerve is reached, when force applied by the retractor exceeds a threshold, when pressure above a certain threshold is applied to a nerve, when a pressure above a certain threshold is applied within a predetermined range of a nerve, when blood oxygenation or blood flow in retracted tissue falls below a certain threshold, etc. Conditions that can trigger an alert by the controller 1306 can be based, at least in part, on the type of sensor(s) 1308 associated with the retractor 1302.

Figure 14:
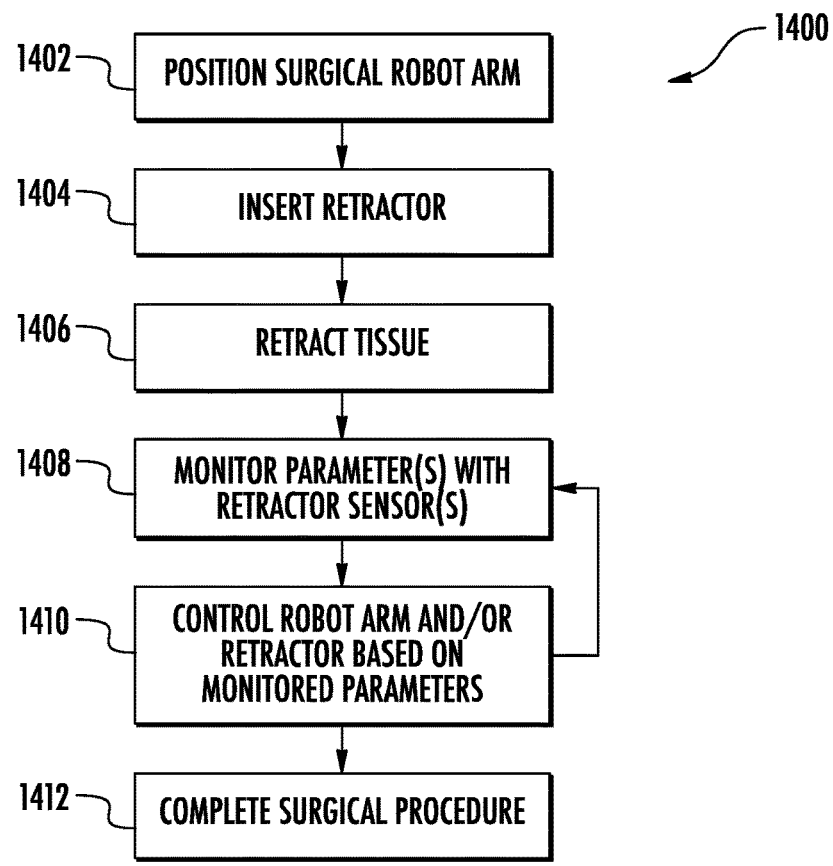
FIG. 14 is a flowchart of a surgical method according to the present disclosure.

FIG. 14 illustrates one embodiment of a method 1400 according to the present disclosure performed in conjunction with a robotic or robot-assisted surgical procedure. The method generally includes positioning a surgical robot arm 1402, inserting a sensor-enabled retractor to a surgical site 1404, retracting a tissue 1406, monitoring one or more parameters with the one or more sensors associated with the retractor 1408, controlling the robot arm and/or the retractor to make fine (e.g., minor) adjustments based on the parameters 1410, and completing the surgical procedure 1412. The monitoring parameters 1408 and controlling the robot arm and/or the retractor 1410 can be repeated a plurality of times as necessary over the course of the surgical procedure.

The method 1400 can be performed with any of the systems and devices described herein. For example, positioning the surgical robot arm 1402 can include moving the surgical robot arm such that the sensor-enabled retractor coupled to the robot arm is located wholly external to a patient but in the vicinity of an incision or an intended incision to a surgical site. The distal end of the retractor can then be inserted 1404 through the incision towards the surgical site to retract tissue 1406 and create or clear the working channel for accessing the surgical site. In some embodiments, instead of making fine (e.g., minor) adjustments based on the parameters, the controller maintains the retractor placement (for example, because a threshold is not met by the parameter(s)).

The one or more sensors associated with the sensor-enabled retractor gather data including a parameter related to retracted anatomy. The parameter data can be transmitted to the controller for monitoring and can be used to assess health of the retracted anatomy. As described above, the controller can output commands to one or both of the robot arm and the retractor based on the parameters to make one or more fine (e.g., minor) adjustments, which can maintain or improve health of the retracted anatomy without interrupting the surgical procedure.

Systems, methods, and devices are disclosed for surgical retraction, e.g., for retracting a portion of an anatomy of a patient at a surgical site ("retracted anatomy"), such as, for example, tissue (e.g., connective tissue, epithelial tissue, muscle tissue, and/or nervous tissue), to provide access to a surgical site in a robotic or robot-assisted surgical procedure. Sensor-enabled surgical retractor devices, along with related systems and methods, are disclosed herein that can be coupled to a surgical robot during a robotic or robot-assisted surgical procedure to maintain health of retracted anatomy and prolong the amount of time until a surgical procedure must be interrupted to adjust (e.g., majorly adjust) a retractor. In some embodiments, interruption of a surgical procedure can be avoided by providing for minor and, in some cases, automatically administered, adjustment of retractor devices to alleviate pressure on retracted tissue without requiring surgeon attention or intervention. Surgical systems of the present disclosure can include a retractor with one or more associated sensors (also referred to herein as a "sensor-enabled retractor"), a surgical robot arm, and a controller.

A variety of sensors can be utilized with the retractor, for example, to determine a parameter relating to the retracted anatomy. Examples of sensors include a force sensor to measure force experienced by retracted anatomy, a pressure sensor to measure pressure experienced by retracted anatomy, an optical sensor (such as, for example, a PPG sensor) to measure blood flow and blood oxygenation of retracted anatomy, a strain gauge which can measure retractor deflection for a pressure and/or force calculation, a torque sensor, a temperature sensor to measure local temperature and/or temperature variations, an ultrasound sensor that can measure changes in anatomical structures (e.g., such as nerves), and a neuromonitoring sensor that can measure nerve health in the retracted anatomy. Combinations thereof are contemplated, for example, in some embodiments, two or more types of associated sensors are employed. The sensors can gather data on one or more parameters relating to at least one of tissue (or other retracted anatomy) at the surgical site. Examples of parameters relating to retracted anatomy include a force exerted on retracted anatomy, a length of time at or above a certain force, a pressure exerted on retracted anatomy, a length of time at or above a certain pressure, blood flow of retracted anatomy, blood oxygenation of retracted anatomy, local temperature and/or temperature variations in retracted anatomy, changes in anatomical structures, and nerve health, and/or combinations thereof.

A controller can receive data from the sensor(s), monitor the one or more parameters to assess a status of the retracted anatomy. The controller can be configured to determine a parameter related to a placement of the retractor. Based on the parameter relating to the status of the retracted anatomy, the controller can determine to output one or more commands to the retractor and/or robot arm to change placement of the retractor, such as, at least one of a three-dimensional position (e.g., depth, latitude, etc.), configuration (e.g., open or closed), rotation, or angulation (e.g., with respect to an initial axis) of the retractor to maintain or improve health of the retracted anatomy without interruption to a surgical procedure being performed. In some embodiments, the command output by the controller can cause adjustment of the retractor position to maintain or improve the measured stress on a nerve. In this manner, fine (e.g., minor) adjustments to the retractor can be made automatically over the course of a surgical procedure to prevent damage to retracted anatomy and increase the time until a major adjustment of the retractor is needed. In some embodiments, a pressure sensor is associated with the retractor to measure stress on a nerve, such as a pressure sensor array extending along a length of the retractor.

In some embodiments, the controller can receive data from the sensor, monitor the one or more parameters to assess a status of the retracted anatomy, and output one or more commands to the retractor to cause an output of energy (e.g., one or more of vibrations, thermal energy, and electrical stimulations from the retractor to tissue in contact with the retractor) from the retractor to maintain or improve the tissue health (e.g., nerve health) at the surgical site.

In some embodiments, the controller can receive data from the sensor, monitor the one or more parameters to assess a status of the retracted anatomy, and output an alert to a user (e.g., surgeon) when nerve health at the surgical site is deteriorating based on the data gathered from the sensor.

Examples of the above-described embodiments can include the following.

In a first example, a surgical retractor system is provided comprising a retractor having a proximal end configured to couple to a surgical robot arm and a distal end for insertion into a surgical site of a patient to retract tissue and provide a working channel, a sensor coupled to the retractor, wherein the sensor is configured to gather data including a parameter related to the retracted tissue, and a controller operatively coupled to the sensor and at least one of the robot arm or the retractor, the controller configured to determine a parameter related to the retractor, receive data from the sensor, and, determine to output at least one of a command to the retractor or a command to the surgical robot arm to stimulate the retracted tissue or to move the retractor to alleviate pressure on the retracted tissue. In this embodiment, the controller command to the surgical robot arm to move the retractor can include a fine adjustment of the retractor placement comprising at least one of a three-dimensional position, configuration, rotation, or angulation to alleviate pressure on the retracted tissue. In this embodiment or the preceding embodiment, the fine adjustment can allow for continued access to the working channel. In any of the preceding embodiments, the controller command to the retractor can cause the retractor to output one or more of vibrations, thermal energy, and electrical stimulations to stimulate the retracted tissue. In any of the preceding embodiments, the controller command to the retractor can cause the retractor to change a diameter of the working channel. In any of the preceding embodiments, the sensor can be mounted on an outer surface of the retractor. In any of the preceding embodiments, the sensor can be a force sensor, a pressure sensor, an optical sensor, a temperature sensor, a strain gauge, a torque sensor, an ultrasound sensor, or a nerve health sensor. In any of the preceding embodiments, at least two different modalities of sensors can be associated with the retractor.

In any of the preceding embodiments, the sensor can be a pressure sensor to measure stress on a nerve. In this embodiment, the sensor can be a pressure sensor array extending along a length of the retractor. In this embodiment or the preceding embodiment, the command output by the controller causes adjustment of the retractor placement to maintain or improve the measured stress on the nerve.

In any of the preceding embodiments, the status of the retracted tissue can comprise a health of the retracted tissue. In this embodiment, the controller can output a command to stimulate or alleviate pressure on the retracted tissue when nerve health at the surgical site is deteriorating based on the data gathered from the sensor. In this embodiment or the preceding embodiment, the controller can output an alert when nerve health at the surgical site is deteriorating based on the data gathered from the sensor.

In any of the preceding embodiments, the retractor can include a plurality of retractor blades, and wherein the command output by the controller can cause the plurality of retractor blades to rotate about a longitudinal axis of the retractor.

In a second example, a surgical method is provided, comprising positioning a surgical robot arm such that a sensor-enabled retractor coupled to the surgical robot arm is in contact with tissue at a surgical site, retracting tissue at the surgical site to create a working channel through tissue in contact with the retractor, monitoring a parameter of the retracted tissue with a sensor coupled to the retractor, and controlling at least one of the robot arm or the retractor based on the monitored parameter during a surgical procedure to improve or maintain retracted tissue health. In this embodiment, the method can further comprise determining to alleviate pressure on the retracted tissue. In this embodiment, a fine adjustment can be made to a parameter of the retractor that does not interrupt access to the working channel. In any of the preceding embodiments, the method can further comprise determining to stimulate the retracted tissue. In any of the preceding embodiments, the method can further comprise controlling the robot arm or the retractor to improve retracted tissue health at intervals of about 30 seconds to about 60 seconds based on a closed-loop feedback of the monitored parameter.

Although specific embodiments are described above, changes can be made within the spirit and scope of the concepts described. For example, while the above embodiments describe a sensor-enabled retractor coupled to a distal end of a robotic arm, in some embodiments, a sensor-enabled retractor of the present disclosure can be coupled or mounted to a holder having one or more robotic or automated device joints. In this manner, the holder can provide for controlled fine (e.g., minor) adjustments of the retractor as described herein, e.g., rotation of the retractor, translation of the retractor, angulation of the retractor, etc. Accordingly, it is intended that this disclosure not be limited to the described embodiments, but have the full scope defined by the language of the claims. The above embodiments describe use of a sensor enabled retractor in a robotic or robot-assisted spinal surgical procedure. While this is one contemplated use, the methods and devices of the present disclosure can be equally adapted for use with other robotic or robot-assisted surgical procedures that require or benefit from retraction of tissue at a surgical site. As such, the devices and components described herein can be formed in a variety of sizes and materials appropriate for use in various robotic or robot-assisted surgical procedures. Further details regarding various surgical systems and methods with which the present disclosure can be implemented can be found in U.S. Ser. No. 16/214,947 (Pat. Pub. No. 2019/0110784, entitled "Systems And Methods For Surgical And Interventional Planning, Support, Post-Operative Follow-Up, And Functional Recovery Tracking"), which is hereby incorporated by reference in its entirety.

It should be noted that any ordering of method expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments, devices, and systems disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices, systems, and methods disclosed herein can be used in minimally-invasive surgery and/or open surgery. While the devices and methods disclosed herein are generally described in the context of orthopedic surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK™ bag. The container and its contents can then be placed in a field of radiation that can penetrate the container, such as gamma radiation, X-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization can be better suited to use with different portions of the device due to the materials utilized, the presence of electrical components, etc.

The embodiments of the present disclosure described above are intended to be merely examples; numerous variations and modifications within the scope of this disclosure. Accordingly, the disclosure is not to be limited by what has been particularly shown and described. All publications and references cited herein are expressly incorporated by reference in their entirety, except for any definitions, subject matter disclaimers or disavowals, and except to the extent that the incorporated material is inconsistent with the express disclosure herein, in which case the language in this disclosure controls.

The invention claimed is:

1. A surgical retractor system, comprising:
   a retractor having a proximal end configured to couple to a surgical robot arm and a distal end for insertion into a surgical site of a patient to retract tissue, wherein an outer surface of the retractor engages the tissue and an inner surface of the retractor defines a working channel;
   a sensor coupled to the outer surface of the retractor, wherein the sensor is configured to gather data including a parameter related to force exerted on a nerve in the retracted tissue; and
   a controller operatively coupled to the sensor and at least one of the robot arm or the retractor, the controller configured to receive data from the sensor, and determine to output at least one of a command to the retractor or a command to the surgical robot arm to:
   stimulate the retracted tissue; or
   move the retractor to alleviate pressure on the retracted tissue.

2. The system of claim 1, wherein the controller command to the surgical robot arm to move the retractor includes a fine adjustment of the retractor placement comprising at least one of a three-dimensional position, configuration, rotation, or angulation to alleviate pressure on the retracted tissue while allowing continued access to the working channel.

3. The system of claim 2, wherein the fine adjustment comprises narrowing the working channel.

4. The system of claim 1, wherein the controller command to the retractor causes the retractor to output one or more of vibrations, thermal energy, and electrical stimulations to stimulate the nerve in the retracted tissue.

5. The system of claim 1, wherein the controller command to the retractor causes the retractor to change a diameter of the working channel.

6. The system of claim 1, wherein the sensor is a force sensor, a pressure sensor, an optical sensor, a temperature sensor, a strain gauge, a torque sensor, an ultrasound sensor, or a nerve health sensor.

7. The system of claim 6, wherein at least two different modalities of sensors are coupled to the outer surface of the retractor.

8. The system of claim 1, wherein the sensor is a pressure sensor to measure stress on the nerve.

9. The system of claim 8, wherein the sensor is a pressure sensor array extending along a length of the retractor.

10. The system of claim 8, wherein the command output by the controller causes adjustment of the retractor placement to maintain or improve the measured stress on the nerve.

11. The system of claim 1, wherein the status of the retracted tissue comprises a health of the nerve in the retracted tissue.

12. The system of claim 11, wherein the controller outputs a command to stimulate or alleviate pressure on the retracted tissue when nerve health at the surgical site is deteriorating based on the data gathered from the sensor.

13. The system of claim 11, wherein the controller outputs an alert when nerve health at the surgical site is deteriorating based on the data gathered from the sensor.

14. The system of claim 1, wherein the retractor includes a plurality of retractor blades, and
wherein the command output by the controller causes the plurality of retractor blades to rotate about a longitudinal axis of the retractor.

15. A surgical method, comprising:
positioning a surgical robot arm such that a sensor-enabled retractor coupled to the surgical robot arm is in contact with tissue at a surgical site;
retracting tissue at the surgical site to create a working channel through tissue in contact with the retractor;
monitoring a parameter of the retracted tissue with a sensor coupled to the retractor; and
controlling at least one of the robot arm or the retractor based on the monitored parameter during a surgical procedure to improve or maintain retracted tissue health by stimulating the retracted tissue with one or more of vibrations, thermal energy, and electrical stimulations from the retractor or moving the retractor to alleviate pressure on a nerve in the retracted tissue while allowing continued access to the working channel.

16. The method of claim 15, further comprising controlling the robot arm or the retractor to improve retracted tissue health at intervals of about 30 seconds to about 60 seconds based on a closed-loop feedback of the monitored parameter.

17. The method of 15, wherein the monitored parameter is a length of time at or above a predefined force exerted by the retractor on the retracted tissue.

18. A surgical retractor system, comprising:
a retractor having a proximal end configured to couple to a surgical robot arm and a distal end for insertion into a surgical site of a patient to retract tissue, wherein an outer surface of the retractor engages the tissue and an inner surface of the retractor defines a working channel;
a sensor coupled to the retractor to gather data relating to a force exerted on the retracted tissue; and
a controller configured to:
determine a length of time at or above a predefined force exerted by the retractor on the retracted tissue, and
upon expiration of the time, to output at least one of a command to the retractor to stimulate the retracted tissue or a command to the surgical robot arm to move the retractor to alleviate pressure on the retracted tissue.

19. The system of claim 18, wherein the retractor stimulates the retracted tissue with one or more of vibrations, thermal energy, and electrical stimulations from the retractor.

20. The system of claim 18, wherein the surgical robot arm to moves the retractor via a fine adjustment to alleviate pressure on the retracted tissue while allowing continued access to the working channel.

* * * * *